US010470663B2

(12) United States Patent
Yasuno et al.

(10) Patent No.: US 10,470,663 B2
(45) Date of Patent: Nov. 12, 2019

(54) JONES MATRIX OCT SYSTEM AND PROGRAM FOR CARRYING OUT IMAGE PROCESSING ON MEASURED DATA OBTAINED BY SAID OCT

(71) Applicant: UNIVERSITY OF TSUKUBA, Tsukuba-shi, Ibaraki (JP)

(72) Inventors: Yoshiaki Yasuno, Tsukuba (JP); Myeong Jin Ju, Tsukuba (JP); Masahide Itoh, Tsukuba (JP)

(73) Assignee: UNIVERSITY OF TSUKUBA, Tsukuba-Shi (JP)

( * ) Notice: Subject to any disclaimer, the term of this patent is extended or adjusted under 35 U.S.C. 154(b) by 982 days.

(21) Appl. No.: 14/892,192

(22) PCT Filed: May 15, 2014

(86) PCT No.: PCT/JP2014/062929

§ 371 (c)(1),
(2) Date: Nov. 18, 2015

(87) PCT Pub. No.: WO2014/188946

PCT Pub. Date: Nov. 27, 2014

(65) Prior Publication Data

US 2016/0106319 A1 Apr. 21, 2016

(30) Foreign Application Priority Data

May 24, 2013 (JP) ................................ 2013-110009

(51) Int. Cl.
*A61B 5/00* (2006.01)
*G01B 9/02* (2006.01)
(Continued)

(52) U.S. Cl.
CPC ............ *A61B 5/0066* (2013.01); *A61B 3/102* (2013.01); *G01B 9/02091* (2013.01);
(Continued)

(58) Field of Classification Search
CPC ............ G01B 9/02091; G01B 2290/35; G01B 2290/45; G01B 2290/70; A61B 3/102; A61B 5/0066; G01N 21/4795
See application file for complete search history.

(56) References Cited

U.S. PATENT DOCUMENTS

| | | | | |
|---|---|---|---|---|
| 9,375,158 B2 * | 6/2016 | Vakoc | .................. | A61B 5/0066 |
| 2007/0086017 A1 * | 4/2007 | Buckland | ............... | A61B 3/102 356/497 |

(Continued)

FOREIGN PATENT DOCUMENTS

| | | |
|---|---|---|
| JP | 11325849 A | 11/1999 |
| JP | 2002310897 A | 10/2002 |

(Continued)

OTHER PUBLICATIONS

Jiao, Shuliang et al. "Jones-matrix imaging of biological tissues with quadruple-channel optical coherence tomography". Journal of Biomedical Optics, vol. 7, No. 3, Jul. 2002, pp. 350-358. (Year: 2002).*

(Continued)

*Primary Examiner* — Michael A Lyons
(74) *Attorney, Agent, or Firm* — Law Office of Katsuhiro Arai

(57) ABSTRACT

A Jones matrix OCT offers improved image stability, image quality, and depth range of image, wherein light from a wavelength-scanning light source is split into two optical paths, and a reference arm is provided along one optical path, while a probe arm that irradiates and reflects light onto the measuring target to generate object light is provided along the other optical path. The probe arm has a polarization delay unit that linearly polarizes the light and then splits it into S-wave component and P-wave component, where the S-wave component and P-wave component are superimposed through optical paths of different optical path lengths,
(Continued)

respectively, after which optical detectors are used to detect different spectral interference beams in the depth direction of the measuring target corresponding to the vertically polarized component and horizontally polarized component, which respectively correspond to the S-wave component and P-wave component, to obtain four spectral interference signals.

9 Claims, 5 Drawing Sheets

(51) Int. Cl.
*G01N 21/47* (2006.01)
*A61B 3/10* (2006.01)

(52) U.S. Cl.
CPC .. *G01N 21/4795* (2013.01); *A61B 2560/0223* (2013.01); *A61B 2562/0242* (2013.01); *A61B 2576/00* (2013.01); *G01B 2290/35* (2013.01); *G01B 2290/45* (2013.01); *G01B 2290/70* (2013.01)

(56) References Cited

U.S. PATENT DOCUMENTS

| | | | | | |
|---|---|---|---|---|---|
| 2007/0236700 | A1* | 10/2007 | Yun | G01N 21/4795 356/491 |
| 2012/0099113 | A1* | 4/2012 | de Boer | A61B 5/0066 356/491 |
| 2012/0327423 | A1 | 12/2012 | Hanebuchi | |
| 2013/0185023 | A1* | 7/2013 | Vakoc | A61B 3/102 702/189 |

FOREIGN PATENT DOCUMENTS

| | | | |
|---|---|---|---|
| JP | 2004028970 | A | 1/2004 |
| JP | 4344829 | B2 | 7/2009 |
| JP | 2009165710 | A | 7/2009 |
| JP | 2010014514 | A | 1/2010 |
| JP | 2012508380 | A | 4/2012 |

OTHER PUBLICATIONS

Baumann,B. et.al., Swept—source/Fourier domain polarization sensitive optical coherence tomography with a passive polarization delay unit, Optics Express, vol. 20, No. 9, Apr. 19, 2012,10229-10241.

Hendargo,H.C. et.al., Automated non-rigid registration and mosaicing for robust imaging of distinct retinal capillary beds using speckle variance optical coherence tomography, Biomedical Optics Express, vol. 4, No. 6, May 7, 2013, 803-821.

International Search Report (ISR) dated Jun. 10, 2014, issued for International application No. PCT/JP2014/062929.

Ju,M.J. et.al., Advanced multi-contrast Jones matrix optical coherence tomography for Doppler and polarization sensitive imaging, Optics Express, vol. 21, No. 16, Aug. 9, 2013, 19412-19436.

Kurokawa,K. et.al., Three-dimensional retinal and choroidal capillary imaging by power Doppler optical coherence angiography with adaptive optics, Optics Express, vol. 20,No. 20, Sep. 20, 2012, 22796-22812.

Makita, et al., Optical Coherence Angigraphy, Optics Express, Aug. 21, 2006, vol. 14, No. 17, 7821-7840.

Yamanari,M. et.al., Polarization-sensitive swept-source optical coherence tomography with continuous source polarization modulation, Optics Express, vol. 16, No. 8, Apr. 11, 2008, 5892-5906.

* cited by examiner

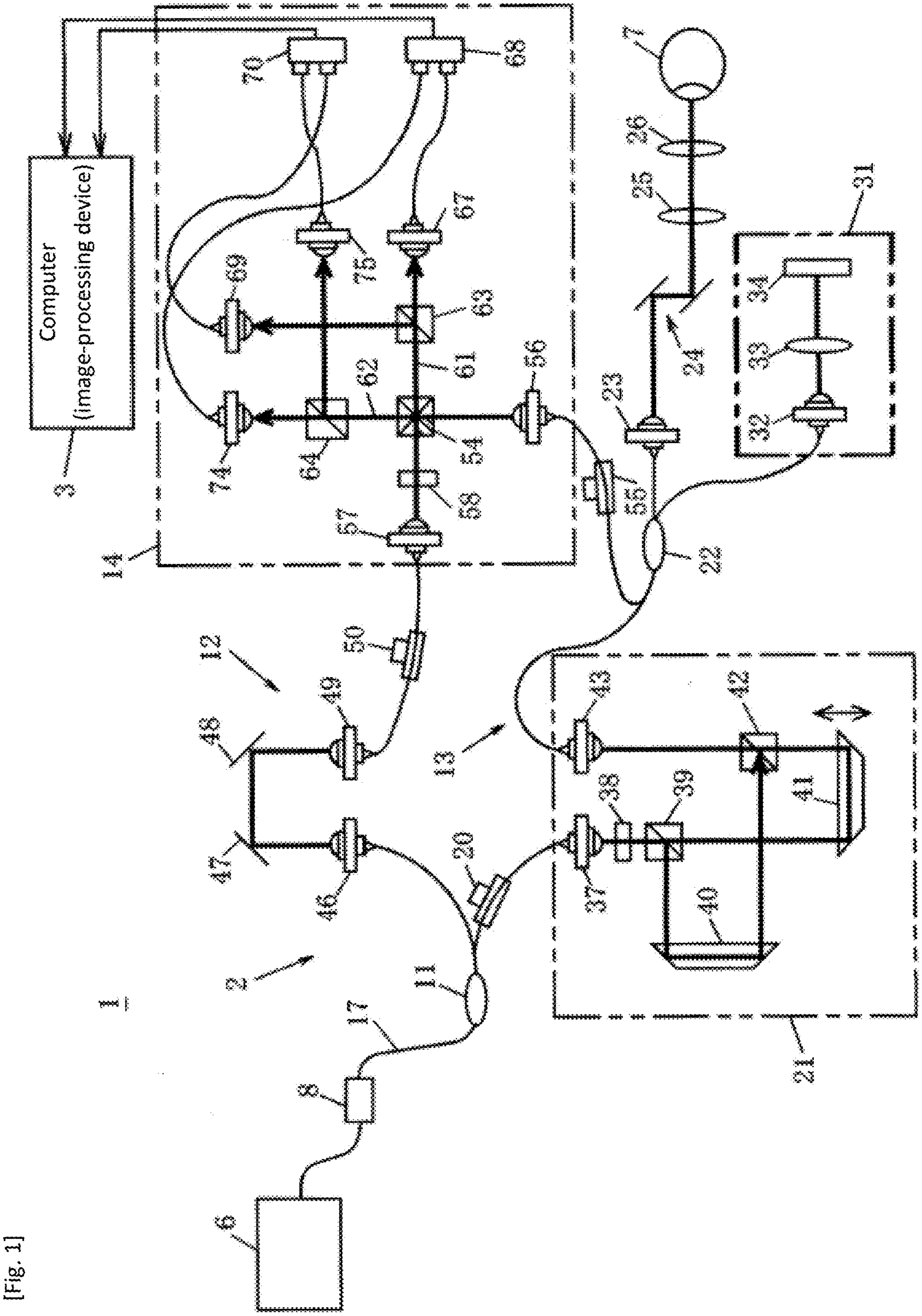
[Fig. 1]

[Fig. 2]
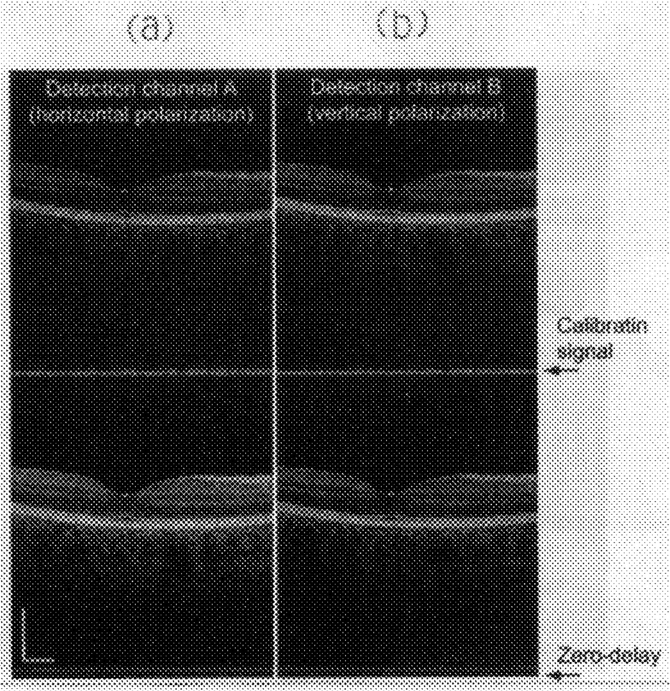

[Fig. 3]
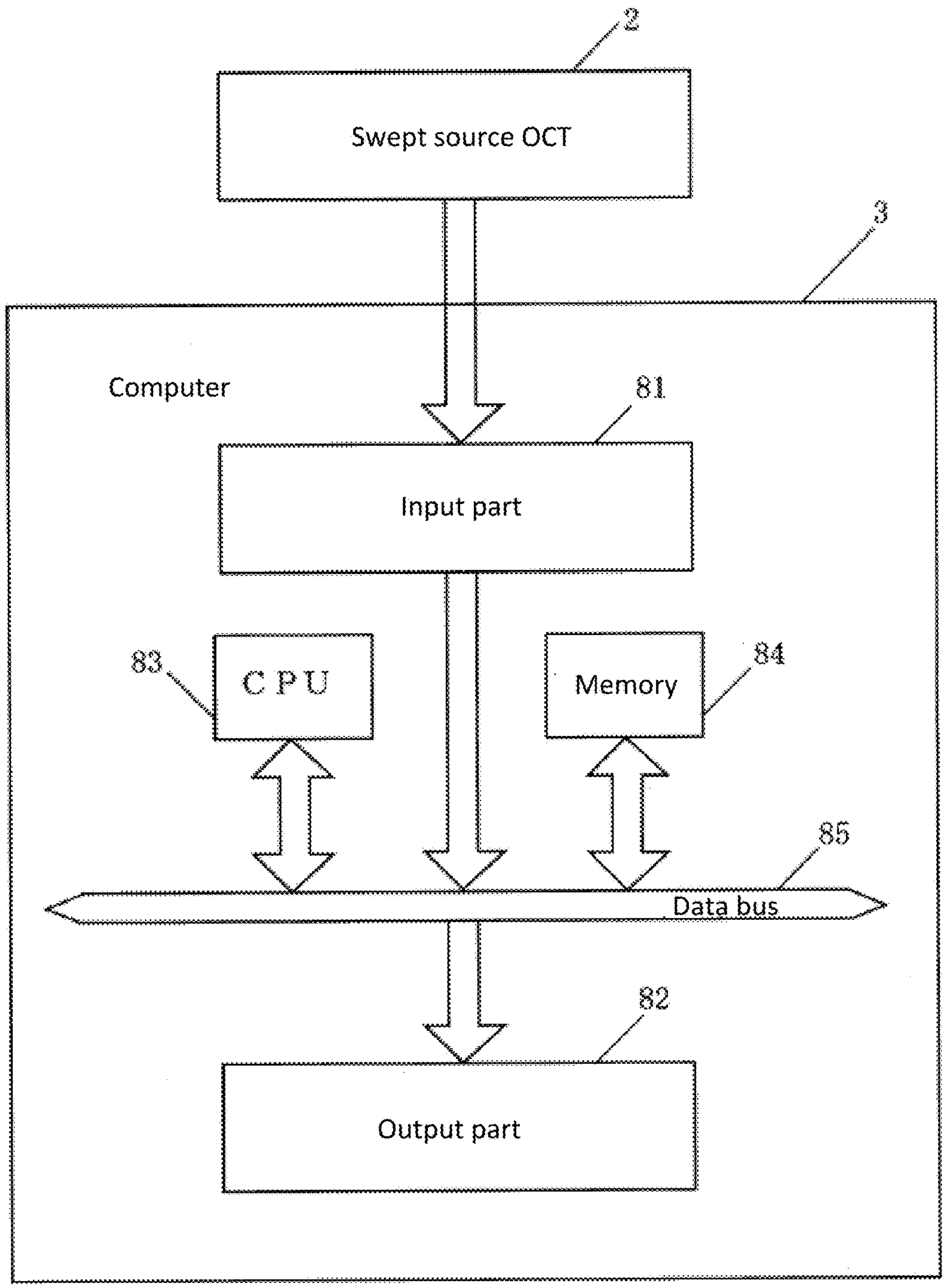

[Fig. 4]
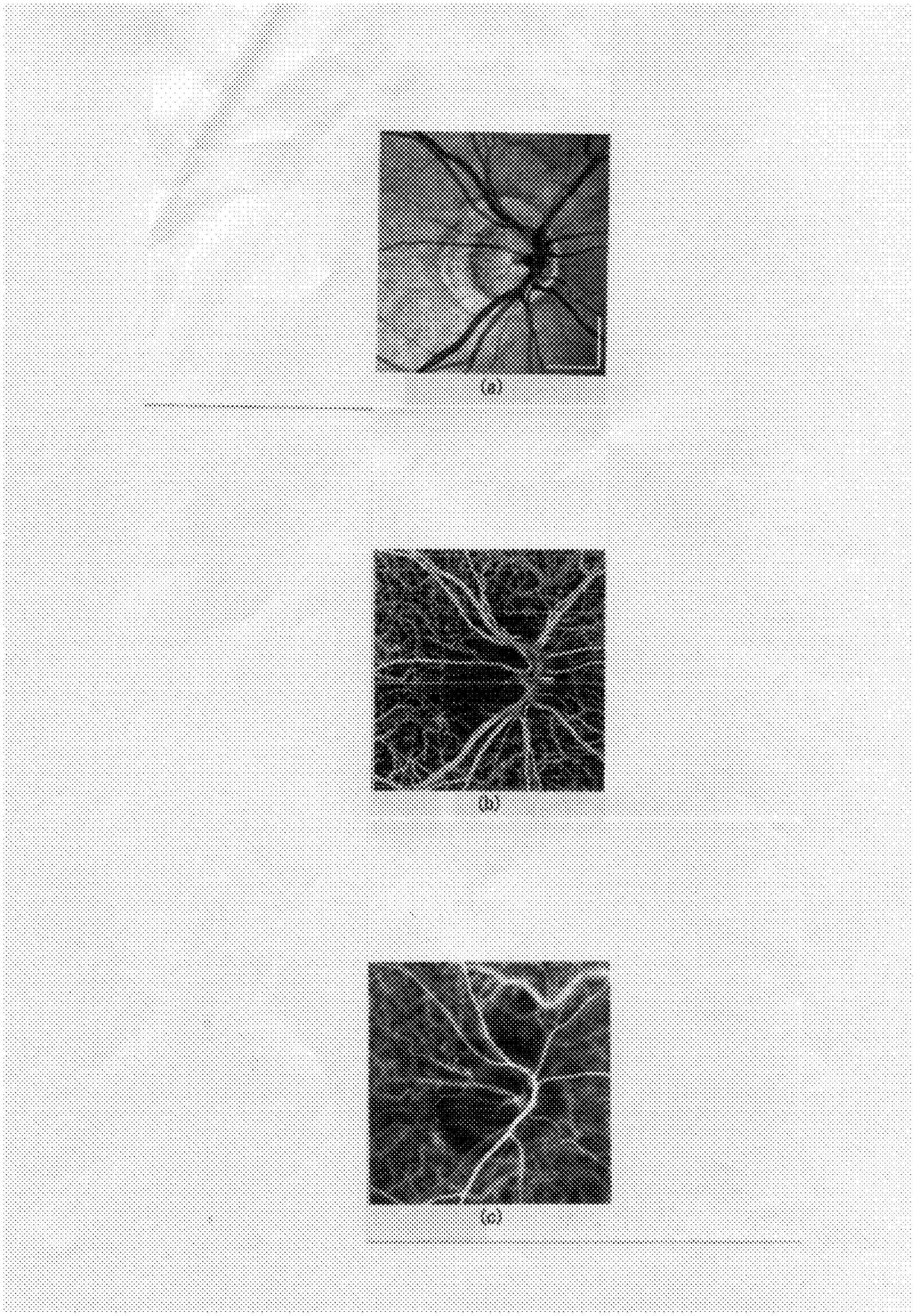

[Fig. 5]
Background Art
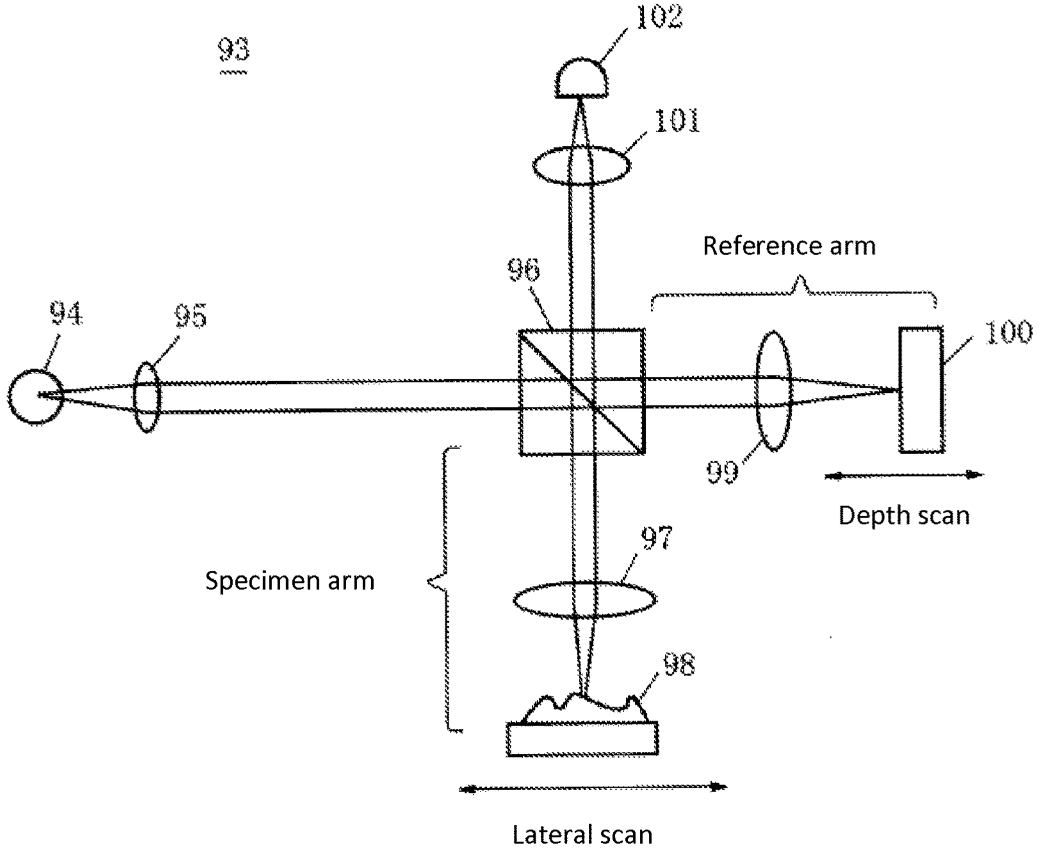

JONES MATRIX OCT SYSTEM AND PROGRAM FOR CARRYING OUT IMAGE PROCESSING ON MEASURED DATA OBTAINED BY SAID OCT

This application is the U.S. National Phase under 35 U.S.C. § 371 of International Application PCT/JP2014/062929, filed May 15, 2014, which claims priority to Japanese Patent Application No. 2013-110009, filed May 24, 2013. The International Application was published under PCT Article 21(2) in a language other than English.

TECHNICAL FIELD

The present invention relates to an image-processing technology for optical coherence tomography (OCT) images in the field of optical interference measuring technology, and more specifically to a Jones matrix OCT system utilizing the Jones matrix, as well as a program for image-processing measured data obtained by such OCT.

BACKGROUND ART

One non-destructive tomographic measuring technology that has been used in the medical field, etc., is an optical coherence tomography (OCT) that uses temporally low coherence light as a probe (refer to Patent Literature 1). The OCT, as it uses light as a measuring probe, has the advantage of being able to measure the refractive index distribution, spectrometric information, polarization information (double-refractive index distribution), etc., of the measuring target.

Also, its ability to visualize as images the section structure and three-dimensional structure of a living organism at a resolution of approx. 2 to 15 μm in a non-invasive manner with high contrast makes the OCT popular in the fields of ophthalmology, dermatology, dentistry, gastroenterology, cardiology, etc.

The basic OCT 93 is based on Michelson's interferometer and its principles are explained using FIG. 5. The light output from a light source 94 is parallelized by a collimator lens 95 and then split into reference light and object light by a beam splitter 96. The object light is condensed onto a measuring target 98 via an objective lens 97 inside the object arm, where the light is scattered and reflected and travels back to the objective lens 97 and beam splitter 96.

On the other hand, the reference light passes through an objective lens 99 inside the reference atm and then is reflected by a reference mirror 100 and travels back to the beam splitter 96 through the objective lens 99. The reference light, now back at the beam splitter 96, enters the condensing lens 101 together with the object light to be condensed onto an optical detector 102 (photodiode, etc.).

For the OCT light source 94, a source of temporally low coherence light (type of light that almost never interferes with another light output from the same light source at a different point in time) is used. With Michelson's interferometer that uses a temporally low coherence light as its light source, interference signals appear only when the distance from the reference arm and that from the object arm are roughly equal. As a result, measuring the interference signal intensity using the optical detector 102 while changing the differential optical path length (τ) between the reference arm and object arm gives interference signals relative to the differential optical path length (interferogram).

The shape of this interferogram represents the reflectance distribution in the depth direction of the measuring target 98, where the structure of the measuring target 98 in the depth direction can be obtained by one-dimensional axial scan. As described above, the OCT 93 allows for measurement of the structure of the measuring target 98 in the depth direction by means of optical path length scan.

This axial scan may be combined with lateral mechanical scan to obtain two-dimensional tomographic images of the measuring target using the resulting two-dimensional scan. The scanning device with which to perform this lateral scan may be constituted so that the measuring target is moved directly, or it may be constituted so that the objective lens is shifted while the target remains fixed, or it may be constituted so that both the measuring target and objective lens remain fixed while the galvano-mirror positioned near the pupillary surface of the objective lens is angularly rotated, or the like.

Extended forms of the aforementioned basic OCT are the spectral domain OCT (SD-OCT) where a spectrometer is used to obtain spectral signals, and the swept source OCT (SS-OCT) designed to obtain spectral interference signals by scanning the wavelength of the light source. The SD-OCT is classified into the Fourier domain OCT (ED-OCT; refer to Patent Literature 2) and the polarization-sensitive OCT (PS-OCT; refer to Patent Literature 3).

The FD-OCT is characterized in that the wavelength spectra of reflected light from the measuring target are obtained using a spectrometer, after which the obtained spectral intensity distribution is Fourier-transformed to retrieve the signals in the real space (OCT signal space), and with this FD-OCT, the tomographic structure of the measuring target can be measured by scanning it in the x-axis direction, without scanning it in the depth direction.

The SS-OCT obtains three-dimensional optical tomographic images by changing the wavelength of the light source using a high-speed wavelength-scanning laser and then rearranging interference signals and thus processing the signals using the light source scan signals synchronously obtained by the spectral signals. One using a monochrome meter as the means for changing the wavelength of the light source can also be used as the SS-OCT.

The PS-OCT is similar to the Fourier domain OCT in that the wavelength spectra of reflected light from the measuring target are obtained using a spectrometer, but the optical coherence tomographic device for PS-OCT allows for measurement of a finer structure of the specimen and isotropy of its refractive index by capturing polarization information of the specimen (measuring target) (refer to Patent Literature 3).

To explain in greater detail, the PS-OCT is designed to successively modulate the polarized state of the beam that has been linearly polarized at the same time as B-scan, wherein the incident light and reference light are horizontally and linearly polarized, vertically and linearly polarized, linearly polarized at 45°, or circularly polarized, through a ½ wavelength plate, ¼ wavelength plate, etc., respectively, after which the reflected light from the measuring target and reference light are superimposed onto each other and caused to interfere with each other by entering only the horizontally polarized component, for example, of each light into the spectrometer through a ½ wavelength plate, ¼ wavelength plate, etc., so that only the component of the object light in the specified polarized state is retrieved and Fourier-transformed. This PS-OCT does not require scan in the depth direction, either.

The Doppler optical coherence tomography (Doppler OCT) has been known as a type of OCT suitable for ophthalmological examination involving non-invasive measurement of in-vivo blood flows, especially blood flows at the back of the eye (blood flows in the retina), and also suitable as a means for cancer and brain imaging (refer to Patent Literature 4).

The Doppler OCT provides a means for measuring the distribution of blood flows, etc., using the aforementioned FD-OCT, etc., and similarly allows for observation of the dimensional vascular channel structure of the retina by producing cross-sectional retinal blood flow images using the spectral domain OCT.

Another known mode of OCT is one using the Jones matrix (Jones matrix OCT) (refer to Patent Literature 5). In particular, an OCT that uses a fiber to produce Doppler and polarization images is known (Non-patent Literature 1).

BACKGROUND ART LITERATURE

Patent Literature

Patent Literature 1: Japanese Patent Laid-open No. 2002-310897
Patent Literature 2: Japanese Patent Laid-open No. Hei 11-325849
Patent Literature 3: Japanese Patent Laid-open No. 2004-028970
Patent Literature 4: Japanese Patent Laid-open No. 2009-165710
Patent Literature 5: Japanese Patent No. 4344829

Non-Patent Literature

Non-patent Literature 1: Makita, Shuichi, Youngjoo Hong, Masahiro Yamanari, Toyohiko Yatagai, and Yoshiaki Yasuno. ⌈Optical Coherence Angigraphy.⌋ Optics Express 14, no. 17 (2006):7821-7840

SUMMARY OF THE INVENTION

Problems to be Solved by the Invention

The conventional types of OCT such as the PS-OCT that utilize polarization have a relatively shallow measurable depth range compared to other types of OCT not utilizing polarization, and are thus subject to low image stability and image quality that limit the use of such OCT in medical examination.

Also, use of the Doppler OCT allows for selective visualization of blood vessels at the back of the eye, but the images as obtained through the Doppler OCT have relatively low contrast and only give simulated images.

An object of the present invention is to solve the conventional problems mentioned above and realize a Jones matrix OCT offering improved image stability, image quality, and depth range of image.

Means for Solving the Problems

To achieve the aforementioned object, the present invention provides a Jones matrix OCT system having: a wavelength-scanning light source; a coupler that splits the light from the wavelength-scanning light source into two optical paths; a reference arm provided along one of the two optical paths, to reflect one split light using a reference mirror and thus generate reference light; a probe arm provided along the other of the two optical paths, to irradiate and reflect the other split light onto the measuring target and thus generate object light; a polarization-separation detection unit that superimposes the reference light and object light to generate spectral interference beams and then detects the spectral interference beams using optical detectors; and a computer that generates tomographic images of the measuring target based on the spectral interference beams detected by the polarization-separation detection unit; wherein the Jones matrix OCT system is characterized in that: the probe arm has a polarization delay unit that linearly polarizes the other light and then splits it into S-wave component and P-wave component, where the S-wave component and P-wave component are superimposed with each other through optical paths of different optical path lengths, respectively; the polarization-separation detection unit can obtain four spectral interference signals by using the optical detectors to detect the different spectral interference beams in the depth direction of the measuring target that correspond to the S-wave component and P-wave component, respectively, among the vertically polarized components of the spectral interference beams, as well as the different spectral interference beams in the depth direction of the measuring target that correspond to the S-wave component and P-wave component, respectively, among the horizontally polarized components; and the computer can generate different tomographic images in the depth z direction of the measuring target from the four spectral interference signals, and also generate tomographic images of higher resolution by obtaining the coherent coupling Eout (z) according to the formula (Mathematical Formula 1) below from a matrix of the four spectral interference signals and, because $\theta_1$ to $\theta_3$ in the formula (Mathematical Formula 1) are expressed by the formula (Mathematical Formula 2) below, by also using these $\theta_1$ to $\theta_3$ to obtain coherent elements of the matrix as shown by the formula (Mathematical Formula 3) below that have been combined after de-randomizing the phases of the four spectral interference signals, further from the formula (Mathematical Formula 1).

$$E_{out}(z) = \begin{bmatrix} E^{(1)}_{outA}(z) & E^{(2)}_{outA}(z) \\ E^{(1)}_{outB}(z) & E^{(2)}_{outB}(z) \end{bmatrix} \simeq \begin{bmatrix} E^{(1)}_{outA}(z) & e^{j\theta_1} E^{(1)}_{outA}(z) \\ e^{j\theta_2} E^{(1)}_{outA}(z) & e^{j\theta_3} E^{(1)}_{outA}(z) \end{bmatrix}$$ [Mathematical Formula 1]

Here, $E^{(1)}_{outA}$ (z) is an OCT section image signal corresponding to the horizontal polarization and P-wave component, $E^{(2)}_{outA}$ (z) is an OCT section image signal corresponding to the horizontal polarization and S-wave component, $E^{(1)}_{outB}$ (z) is an OCT section image signal corresponding to the vertical polarization and P-wave component, and $E^{(2)}_{outB}$ (z) is an OCT section image signal corresponding to the vertical polarization and S-wave component.

$$\theta_1 \equiv \mathrm{Arg}\left[\sum_z E^{(2)}_{outA}(z) E^{(1)}_{outA}(z)^*\right]$$ [Mathematical Formula 2]

$$\theta_2 \equiv \mathrm{Arg}\left[\sum_z E^{(1)}_{outB}(z) E^{(1)}_{outA}(z)^*\right]$$

$$\theta_3 \equiv \mathrm{Arg}\left[\sum_z E^{(2)}_{outB}(z) E^{(1)}_{outA}(z)^*\right]$$

[Mathematical Formula 3]

$$\overline{E_{out}}(z) = \frac{1}{4}\left[E^{(1)}_{outA}(z) + e^{-i\theta_1}E^{(2)}_{outA}(z) + e^{-i\theta_2}E^{(1)}_{outB}(z) + e^{-i\theta_3}E^{(2)}_{outB}(z)\right]$$

The constitution of the computer is such that it can display a Doppler image by calculating the formula (Mathematical Formula 5) below indicating the square intensity of Doppler phase shift, based on the definition that the Doppler shift ΔØ (z,j) between the A-line in the jth B-scan and A-line in the j+1th B-scan is represented by the formula (Mathematical Formula 4) below involving mutually conjugating coherent components, where the same point may be measured with multiple (m number of) B-scans to obtain the Doppler shift ΔØ (z,j) as given by the formula (Mathematical Formula 6) below, which is then applied to Doppler measurement to improve the sensitivity of Doppler measurement.

[Mathematical Formula 4]

$$\Delta\phi(z, j) = \mathrm{Arg}[\overline{E_{out}}(z, j+1)\overline{E_{out}}(z, j)^*]$$

[Mathematical Formula 5]

$$|\overline{\Delta\phi}(z,j)|^2$$

[Mathematical Formula 6]

$$\overline{\Delta\phi}(z, j) = \mathrm{Arg}\left[\sum_{j=m_0}^{m_0+m-2} \overline{E_{out}}(z, j+1)\overline{E_{out}}(z, j)^*\exp(-i\phi_b(j))W(z, j)\right]$$

Here, $m_0$ is a starting B-scan parameter, W (z,j) is an intensity mask defined by the formula (Mathematical Formula 7) below, and $\varepsilon^2$ is a noise floor (minimum noise) of OCT image.

[Mathematical Formula 7]

$$W(z, j) = \begin{cases} 1: & \overline{E_{out}}(z, j+1)\overline{E_{out}}(z, j)^* > \varepsilon^2 \\ 0: & \text{otherwise} \end{cases}.$$

The computer may be constituted in such a way that it can obtain OCT images based on the scattered and reflected light from the measuring target, as the formula (Mathematical Formula 8) below using coherent matrix components, and also obtain high-quality scattered OCT images according to the formula (Mathematical Formula 9) below by calculating a coherent average of data from multiple B-scans.

[Mathematical Formula 8]

$$\bar{I}(z,j)=|\overline{E_{out}}(z,j)|^2$$

[Mathematical Formula 9]

$$\bar{I}(z, j) = \sum_{j=m_0}^{m_0+m-1} \overline{E_{out}}(z, j)\exp(-i\phi_b(j))$$

Desirably the constitution is such that: a phase calibration unit having a calibration mirror is provided in the optical path branching from the optical path leading to the measuring target via the coupler; the calibration mirror reflects the interference beams entering the calibration unit, which have been generated at the polarization delay unit due to interference caused by the differential optical path length with respect to the P waves or S waves themselves, and sends the interference beams to the polarization-separation detection unit via the coupler to be superimposed with the reference light into interference beams that function as calibration signals; the horizontal-balancing polarization detector and vertical-balancing polarization detector respectively detect the interference beams that function as calibration signals; and the computer uses these calibration signals to compensate the jitter generating in the synchronization between the scanning of the wavelength of the light source and A-scan.

To achieve the aforementioned object, the present invention provides a program installed in a computer of a Jones matrix OCT system to generate tomographic images of a measuring target based on the spectral interference beams detected by an optical detector, where the Jones matrix OCT system has: a wavelength-scanning light source; a coupler that splits the light output from the wavelength-scanning light source into two optical paths; a reference arm provided along one of the two optical paths, to reflect one split light using a reference mirror and thus generate reference light; a probe arm provided along the other of the two optical paths, to irradiate and reflect the other split light onto the measuring target and thus generate object light; a polarization-separation detection unit that superimposes the reference light and object light to generate spectral interference beams and then detects the spectral interference beams using optical detectors; and a computer; wherein the probe arm has a polarization delay unit that linearly polarizes the other light and then splits it into S-wave component and P-wave component, where the S-wave component and P-wave component are superimposed with each other through optical paths of different optical path lengths, respectively; the polarization-separation detection unit can obtain four spectral interference signals by using the optical detectors to detect the different spectral interference beams in the depth direction of the measuring target that correspond to the S-wave component and P-wave component, respectively, among the vertically polarized components of the spectral interference beams, as well as the different spectral interference beams in the depth direction of the measuring target that correspond to the S-wave component and P-wave component, respectively, among the horizontally polarized components; and the program is characterized in that it allows the computer to function as an image-processing means that can generate different tomographic images in the depth z direction of the measuring target from the four spectral interference signals, and also generate tomographic images of higher resolution by obtaining the coherent coupling Eout (z) according to the formula (Mathematical Formula 10) below from a matrix of the four spectral interference signals and, because $\theta_1$ to $\theta_3$ in the formula (Mathematical Formula 10) are expressed by the formula (Mathematical Formula 11) below, by also using these $\theta_1$ to $\theta_3$ to obtain coherent elements of the matrix as shown by the formula (Mathematical Formula 12) below that have been combined after de-randomizing the phases of the four spectral interference signals, further from the formula (Mathematical Formula 10).

[Mathematical Formula 10]

$$E_{out}(z) = \begin{bmatrix} E^{(1)}_{outA}(z) & E^{(2)}_{outA}(z) \\ E^{(1)}_{outB}(z) & E^{(2)}_{outB}(z) \end{bmatrix} \simeq \begin{bmatrix} E^{(1)}_{outA}(z) & e^{j\theta_1}E^{(1)}_{outA}(z) \\ e^{j\theta_2}E^{(1)}_{outA}(z) & e^{j\theta_3}E^{(1)}_{outA}(z) \end{bmatrix}$$

Here, $E^{(1)}_{outA}$ (z) is an OCT section image signal corresponding to the horizontal polarization and P-wave component, $E^{(2)}_{outA}$ (z) is an OCT section image signal corresponding to the horizontal polarization and S-wave component, $E^{(1)}_{outB}$ (z) is an OCT section image signal corresponding to the vertical polarization and P-wave component, and $E^{(2)}_{outB}$ (z) is an OCT section image signal corresponding to the vertical polarization and S-wave component.

$$\theta_1 \equiv \mathrm{Arg}\left[\sum_z E^{(2)}_{outA}(z)E^{(1)}_{outA}(z)^*\right]$$ [Mathematical Formula 11]

$$\theta_2 \equiv \mathrm{Arg}\left[\sum_z E^{(1)}_{outB}(z)E^{(1)}_{outA}(z)^*\right]$$

$$\theta_3 \equiv \mathrm{Arg}\left[\sum_z E^{(2)}_{outB}(z)E^{(1)}_{outA}(z)^*\right]$$

$$\overline{E_{out}}(z) = \frac{1}{4}[E^{(1)}_{outA}(z) + e^{-i\theta_1}E^{(2)}_{outA}(z) + e^{-i\theta_2}E^{(1)}_{outB}(z) + e^{-i\theta_3}E^{(2)}_{outB}(z)]$$ [Mathematical Formula 12]

Desirably the constitution of the program pertaining to the present invention is such that it allows the computer to function as an image-processing means that can display a Doppler image by calculating the formula (Mathematical Formula 14) below indicating the square intensity of Doppler phase shift, based on the definition that the Doppler shift ΔØ (z,j) between the A-line in the jth B-scan and A-line in the j+1th B-scan is represented by the formula (Mathematical Formula 13) below involving mutually conjugating coherent components, and also improves the sensitivity of Doppler measurement by measuring the same point with multiple (m number of) B-scans to obtain the Doppler shift ΔØ (z,j) as given by the formula (Mathematical Formula 15) below, which is then applied to Doppler measurement.

$$\Delta\phi(z, j) = \mathrm{Arg}[\overline{E_{out}}(z, j+1)\overline{E_{out}}(z, j)^*]$$ [Mathematical Formula 13]

$$|\overline{\Delta\phi}(z,j)|^2$$ [Mathematical Formula 14]

$$\overline{\Delta\phi}(z, j) = \mathrm{Arg}\left[\sum_{j=m_0}^{m_0+m-2} \overline{E_{out}}(z, j+1)\overline{E_{out}}(z, j)^*\exp(-i\phi_b(j))W(z, j)\right]$$ [Mathematical Formula 15]

Here, $m_0$ is a starting B-scan parameter, W (z,j) is an intensity mask defined by the formula (Mathematical Formula 16) below, and $\varepsilon^2$ is a noise floor (minimum noise) of OCT image.

$$W(z, j) = \begin{cases} 1: & \overline{E_{out}}(z, j+1)\overline{E_{out}}(z, j)^* > \varepsilon^2 \\ 0: & \text{otherwise} \end{cases}.$$ [Mathematical Formula 16]

Desirably the program pertaining to the present invention allows the computer to function as an image-processing means that can obtain OCT images based on the scattered and reflected light from the measuring target, as the formula (Mathematical Formula 17) below using coherent matrix components, and also obtain high-quality scattered OCT images according to the formula (Mathematical Formula 18) below by calculating a coherent average of data from multiple B-scans.

$$\bar{I}(z,j) = |\overline{E_{out}}(z,j)|^2$$ [Mathematical Formula 17]

$$\bar{I}(z, j) = \sum_{j=m_0}^{m_0+m-1} \overline{E_{out}}(z, j)\exp(-i\phi_b(j))$$ [Mathematical Formula 18]

Effects of the Invention

According to the Jones matrix OCT system pertaining to the present invention, as well as the program for image-processing the measured data obtained by such OCT, the quality of images obtained by the Jones matrix OCT can be improved, while at the same time improved images can be obtained over, for example, deeper ranges of the measuring target such as the choroid membrane at the back of the eye.

In particular, high-contrast images can be obtained by applying the present invention to an OCT with Doppler function. Because of this, image information of higher resolution, compared to image information by ophthalmography in ophthalmological diagnosis, for example, that could only heretofore be obtained invasively, can be obtained in a non-invasive manner to allow for quantitative evaluation of the blood vessels at the back of the eye, or the like.

BRIEF DESCRIPTION OF THE DRAWINGS

FIG. 1 Diagram showing the overall constitution of the OCT device in an example of the Jones matrix OCT system pertaining to the present invention.

[FIG. 2] OCT tomographic images (a) and (b) based on interference beams that correspond, respectively, to the S wave and P wave received by the horizontal-balancing polarization detector and vertical-balancing polarization detector of the OCT device in the above example.

FIG. 3 Diagram showing the computer that performs image-processing in the OCT system in the above example.

FIG. 4 (*a*) is a tomographic image showing the choroidal vessels obtained by the Jones matrix OCT system in the above example; (*b*) is a tomographic image showing the choroidal vessels obtained by applying the present invention to an OCT with Doppler function; and (*c*) is a comparative example and contrast image showing the same choroidal vessels obtained by angiography of the conventional indocyanine green angiography (ICGA) type.

FIG. 5 Diagram explaining the conventional basic OCT.

MODE FOR CARRYING OUT THE INVENTION

The mode for carrying out the Jones matrix optical coherence tomography (Jones matrix OCT; OCT where OCT-obtained interference signals are processed using the Jones matrix means to obtain images) system pertaining to the present invention, and the program for image-processing the image data obtained by such OCT, is explained below according to the example and by referring to the drawings.

EXAMPLE

FIG. 1 is a diagram showing the overall constitution of a Jones matrix OCT system 1 pertaining to the present invention. As shown in FIG. 1, the Jones matrix OCT system 1 pertaining to the present invention has an optical image measuring device (OCT device) 2, and a computer 3 for image-processing the image data obtained by the optical image measuring device (OCT device) 2.

Under the present invention, the optical image measuring device (OCT device) 2 can be applied to general OCT data processing utilizing polarization, one example of which is explained in this example based on the constitution of a swept source OCT, as the optical image measuring device (OCT device) 2, involving scanning of the wavelength of the light source to obtain spectral interference signals (swept source OCT (SS-OCT); hereinafter denoted by 2).

Then, the image-processing program pertaining to the present invention allows the computer 3 to function as a means for image-processing the image data obtained by the swept source OCT 2.

(OCT Device)

Under the present invention, the swept source OCT 2 is such that the beam from a light source 6 is split and one beam is linearly polarized and split into S wave (S wave polarization) and P wave (P wave polarization), which are then irradiated as incident beams of different optical path lengths, respectively, to scan a measuring target 7 (B-scan) to obtain light reflected by the target (object light), while using the other beam as reference light, to perform OCT measurement based on spectral interference of the two.

It should be noted that, in the Specification herein, A-scan refers to a scan of the measuring target 7 in the depth direction (or irradiation of measurement beam in reality), and data obtained by A-scan is referred to as "A-line data" or "A-line," for short. B-scan refers to a scan in the direction perpendicular to the depth direction of the measuring target 7.

The present invention is also characterized by having a multi-contrast OCT constitution where, among the spectral interference components based on S wave and P wave, respectively, the horizontally polarized component (H) and vertically polarized component (V) are measured with the balancing polarization detector to obtain Jones vectors representing the four polarization characteristics of the measuring target 7 (H images based on S wave and P wave, respectively, and V images based on S wave and P wave, respectively).

The swept source OCT 2 has a light source 6, optical isolator 8 (device with a function to transmit light only in one direction and shield light in the opposite direction), fiber coupler 11 (optical coupler), reference arm 12, probe arm 13 (arm for measuring target), polarization-separation detection unit 14 and other optical elements.

In the optics of this swept source OCT 2, the optical elements are connected to each other by fibers 17; however, a type of structure where they are not connected by fibers 17 (free-space type) is also permitted.

For the light source 6, which is a wavelength-scanning light source 6 for wavelength scanning, a super luminescent diode (SLD) is used.

The probe arm 13 is constituted by a polarization controller 20, polarization delay unit 21, coupler 22, fiber collimator 23, two-axis galvano-scanner 24, objective lens 25, and non-spherical ophthalmological lens 26, which are arranged in this order in the optical path of the arm.

Connected to the coupler 22 is a phase calibration unit 31 branching from the optical path to the measuring target 7. The phase calibration unit 31 has a fiber collimator 32, lens 33, and mirror (calibration mirror) 34.

The polarization delay unit 21 has a fiber collimator 37, 45° linear polarizer 38, polarization beam splitter 39, first Dove prism 40, and second Dove prism 41 respectively positioned along the two optical paths split from this polarization beam splitter 39, multiplexing polarization beam splitter 42, and fiber collimator 43.

The "Dove prism" is a prism corresponding to one-half a right-angle prism, designed to reflect internally a parallel beam received on a square triangle slope and then output the beam in parallel with the incident direction of the beam. The first Dove prism 40 is fixed at a certain position, and the optical path length from the polarization beam splitter 39 to the multiplexing polarization beam splitter 42, via the first Dove prism 40, is constant.

The second Dove prism 41 is a prism for adjusting optical path length, provided in a manner movable in the direction of optical path. By moving it in the direction of optical path as deemed appropriate, the optical path length from the polarization beam splitter 39 to the multiplexing polarization beam splitter 42, via the second Dove prism 42, can be adjusted.

The reference arm 12 is constituted by a fiber collimator 46, mirror 47, mirror 48, fiber collimator 49, and polarization controller 50, which are arranged in this order along the optical path of the arm.

The polarization-separation detection unit 14 has a multiplexing beam splitter 54 connected to a fiber collimator 56 which in turn is connected to the polarization controller 55 positioned along one optical path from the probe arm 13 on the incident side of the multiplexing beam splitter 54, and also has a fiber collimator 57 and 45° linear polarizer 58 connected in this order to the other optical path from the reference arm 12.

The polarization-separation detection unit 14 has a first optical path 61 and second optical path 62 along which split beams are transmitted on the output side of the multiplexing beam splitter 54. A first polarization beam splitter 63 is provided along the first optical path 61, while a second polarization beam splitter 64 is provided along the second optical path.

A horizontal-balancing polarization detector 68 is connected, via a fiber collimator 67, to the optical path along which a horizontally polarized component split from the first beam splitter 63 is transmitted, while a vertical-balancing polarization detector 70 is connected, via a fiber collimator 69, to the optical path along which a vertically polarized component is transmitted.

Similarly, the horizontal-balancing polarization detector 68 is connected, via a fiber collimator 74, to the optical path along which a horizontally polarized component split from the second beam splitter 64 is transmitted, while the vertical-balancing polarization detector 70 is connected, via a fiber collimator 75, to the optical path along which a vertically polarized component is transmitted.

(Operations)

In the swept source OCT 2 constituted as above, the beam from the light source 6 is separated into the direction of the reference arm 12 and direction of the probe arm 13 at a light quantity ratio of 10% and 90%, respectively, by the fiber coupler 11 via the optical isolator 8. The optical isolator 8 allows the beam to pass through it only in one direction, while shielding the reflected light to protect the light source 6.

The beam separated into the probe arm 13 direction passes through the polarization controller 20 and enters the polarization delay unit 21. At the polarization delay unit 21, the beam passes the fiber collimator 37 and is linearly polarized by the linear polarizer 38, and then is separated by the polarization beam splitter 39 into S waves (reflected polarized component vibrating vertically to the incident plane) and P waves (transmitting polarized component vibrating in parallel with the incident plane) vibrating in the directions perpendicular to each other.

The S-wave beam passes through the first Dove prism 40 and enters the multiplexing polarization beam splitter 42, where the optical path length from the polarization beam splitter 39 to the multiplexing polarization beam splitter 42 is constant.

The P-wave beam passes through the second Dove prism 41 for adjusting optical path length and enters the multiplexing polarization beam splitter 42. With the P-wave beam, the optical path length from the polarization beam splitter 39 to the multiplexing polarization beam splitter 42 can be adjusted by moving the second Dove prism 41 as deemed appropriate in the direction of optical path.

Here, the optical path length of P waves is pre-adjusted longer than the optical path length of S waves. The S-wave beam and P-wave beam, each having a different optical path length, are superimposed onto (multiplexed with) each other at the multiplexing polarization beam splitter 42 in a state of shifted phases, and the resulting beam passes through the fiber collimator 43 and is output toward the coupler 22 from the polarization delay unit 21.

After the beam has entered the coupler 22, 20% of it passes through the fiber collimator 23, two-axis galvanoscanner 24, objective lens 25, and non-spherical ophthalmological lens 26, and then is irradiated onto the measuring target 7 (such as the cornea, retina or choroid membrane of the eye) as probe beam, while the remaining 80% enters the phase calibration unit 31.

The measurement beam that has been irradiated onto and reflected by the measuring target 7, and calibration beam that has been reflected by the calibration mirror 34 of the phase calibration unit 31, return through the probe arm 13, pass through the polarization controller 55 via the coupler 22, enter the polarization-separation detection unit 14, pass through the fiber collimator 56, and enter the multiplexing polarization beam splitter 54.

On the other hand, the reference beam that has entered the reference arm 12 via the coupler passes through the fiber collimator 46, mirror 47, mirror 48, fiber collimator 49, and polarization controller 50, enters the polarization-separation detection unit 14, passes through the fiber collimator 57, is linearly polarized by the linear polarizer 58, and enters the multiplexing polarization beam splitter 54.

The measurement beam and reference beam that have entered the multiplexing polarization beam splitter 54 are superimposed onto and interfere with each other to become interference beams, and these interference beams are transmitted to the first polarization beam splitter 63 along the first optical path 61 and to the second polarization beam splitter 64 along the second optical path 62.

The interference beam that has entered the first polarization beam splitter 63 along the first optical path 61 is separated, at the first polarization beam splitter 63, into a horizontally polarized component and vertically polarized component that are detected by the horizontal-balancing polarization detector 68 and vertical-balancing polarization detector 70, respectively.

The interference beam that has entered the second polarization beam splitter 64 along the second optical path 62 is separated, at the second polarization beam splitter 64, into a horizontally polarized component and vertically polarized component that are detected by the horizontal-balancing polarization detector 68 and vertical-balancing polarization detector 70, respectively.

The interference beam corresponding to P waves and horizontally polarized component of such interference beam, as detected by the horizontal-balancing polarization detector 68, gives a first tomographic image, while at the same time the interference beam corresponding to S waves and horizontally polarized component of such interference beam gives a second tomographic image.

FIG. 2 shows OCT tomographic images of the macular retina being the measuring target 7, where the aforementioned two OCT tomographic images are shown at the top and bottom of FIG. 2 (*a*), respectively. The top tomographic image of FIG. 2 (*a*) is a tomographic image corresponding to S waves, formed on the shallower side of the measuring target 7. On the other hand, the bottom tomographic image of FIG. 2 (*a*) is a second tomographic image corresponding to P waves, formed on the deeper side of the measuring target 7.

The vertical-balancing polarization detector gives a first tomographic image based on the interference beam corresponding to S waves that has been received by one of its receivers and also on the vertically polarized component of such interference beam, as well as a second tomographic image based on the interference beam corresponding to P waves that has been received by the other of its receivers and also on the vertically polarized component of such interference beam.

These two OCT tomographic images are shown at the top and bottom of FIG. 2 (*b*), respectively. The top tomographic image of FIG. 2 (*b*) is a first tomographic image corresponding to S waves, formed on the shallower side of the measuring target 7. On the other hand, the bottom tomographic image of FIG. 2 (*b*) is a second tomographic image corresponding to P waves, formed on the deeper side of the measuring target 7.

As described above, the swept source OCT 2 proposed by the present invention constitutes a multi-contrast OCT that gives four OCT tomographic images. It should be noted that a further characteristic of the system proposed by the present invention is that it has a phase calibration unit 31 on the probe arm 13 side. This is explained below.

At the polarization delay unit 21, a phenomenon occurs where, of the incident beams that have been linearly polarized, some of the P-wave beam (approx. 4.4%) does not transmit through the polarization beam splitter 39 but is reflected and mixes with the S-wave beam, thereby preventing complete separation of the beams.

In other words, ideally the polarization beam splitter 39 of the polarization delay unit 21 lets the P waves transmit through, while reflecting the S waves, but in reality commercially available polarization beam splitters cannot completely separate the linearly polarized beams, and allow the P waves to mix into the reflected light. As a result, the polarization delay unit 21 behaves like Mach-Zehnder interferometers having a differential optical path length $z_d$ with each other, with respect to the P waves, and interference beams that function as calibration signals are generated.

That is to say, this Mach-Zehnder interferometer-like function occurring when the P-wave beam that has transmitted through the polarization beam splitter 39 and the P-wave beam that has mixed into the reflected light are superimposed onto each other at the polarization beam splitter 42, causes interference beams to generate and these beams function as calibration signals.

If the polarization beam splitter is constituted in such a way as to reflect the P waves but let the S waves transmit through, then it is possible to utilize the partial reflection of S waves and mixing of the partially reflected S waves into P waves, to cause the optical path lengths of S waves to differ and thereby generate interference beams that will then function as calibration signals.

The interference beams splitting from the coupler 22 of the probe arm 13 and functioning as calibration signals enter the phase calibration unit 31, travel through the fiber collimator 22, and lens 33, and are reflected by the calibration mirror 34, and these reflected interference beams that function as calibration signals pass through the polarization controller 55 via the coupler 22 and enter the polarization-separation detection unit 14.

The interference beams from the phase calibration unit 31 are superimposed onto, and thereby caused to interfere with, the reference beam at the multiplexing beam splitter 54 of the polarization-separation detection unit 14, and then are split and transmitted to the first optical path 61 and second optical path 62, after which they are further separated into the horizontally polarized component and vertically polarized component at the first polarization beam splitter 63 and second polarization beam splitter 64, respectively. The horizontally polarized component and vertically polarized component are detected by the horizontal-balancing polarization detector 68 and vertical-balancing polarization detector 70, respectively.

In each of FIG. 2 (*a*) and FIG. 2 (*b*), the interference beams generated by the phase calibration unit 31 and functioning as calibration signals form a calibration line image (image denoted by "←Calibration signal" in the figure) at the exact middle point, in the vertical direction, of the tomographic image detected by the horizontal-balancing polarization detector 68 and vertical-balancing polarization detector 70, respectively.

(Image Processing)

The constitution of, and program for, the image-processing means that uses the computer 3 to process the four OCT tomographic images obtained as above are explained below.

The measured data obtained by the swept source OCT of the aforementioned constitution is input to the computer 3 used as an image-processing device. This computer 3 is a normal computer having, as shown in FIG. 3, an input part 81, output part 82, CPU 83, memory 84, and data bus 85.

The program pertaining to the present invention is stored in the memory 84 of the computer 3 and causes the computer 3 to function as a means for more clearly image-processing the images obtained by the swept source OCT 2 and input to the computer 3. By installing this program in the computer 3, the Jones matrix OCT system 1 pertaining to the present invention is equipped with a means for image-processing images more clearly.

Traditionally in the Jones matrix OCT (OCT where the interference signals obtained by the OCT are processed using the Jones matrix means to obtain images), OCT images are obtained by averaging the square intensities of four Jones matrix elements (four OCT tomographic image signals).

Also, the Doppler OCT averages the Doppler phase shift signals of four elements (four OCT tomographic image signals). With these conventional means, a decrease in sensitivity is inevitable due to the separation of the power from the light source into four OCT tomographic image signals, or specifically four Jones matrix elements.

To solve this problem, the present invention is characterized in that it adopts a new type of signal processing to coherently couple (coherent coupling) the four Jones matrix elements (four OCT tomographic image signals) as complex amplitudes (time-free portions of the complex representation of OCT tomographic image signals).

According to the present invention, adoption of this constitution makes it possible to use the scattered OCT signals and Doppler OCT signals measured by the swept source OCT 2, to respectively obtain tomographic image signals through the coherent coupling of four matrix elements (four OCT tomographic image signals).

To be specific, the coherent coupling $E_{out}$ (z) of matrix elements is expressed by the formula (Mathematical Formula 19) below as a matrix of four OCT tomographic image signals expressed by depth (z), namely, $E^{(1)}{}_{outA}$ (z), $E^{(1)}{}_{outB}$ (z), $E^{(2)}{}_{outA}$ (z) and $E^{(2)}{}_{outB}$ (z).

[Mathematical Formula 19]

$$E_{out}(z) = \begin{bmatrix} E^{(1)}_{outA}(z) & E^{(2)}_{outA}(z) \\ E^{(1)}_{outB}(z) & E^{(2)}_{outB}(z) \end{bmatrix} \simeq \begin{bmatrix} E^{(1)}_{outA}(z) & e^{j\theta_1} E^{(1)}_{outA}(z) \\ e^{j\theta_2} E^{(1)}_{outA}(z) & e^{j\theta_3} E^{(1)}_{outA}(z) \end{bmatrix}$$

Here, $E^{(1)}{}_{outA}$(z) is an OCT section image signal corresponding to the horizontal polarization and P-wave component, $E^{(2)}{}_{outA}$ (z) is an OCT section image signal corresponding to the horizontal polarization and S-wave component, $E^{(1)}{}_{outB}$ (z) is an OCT section image signal corresponding to the vertical polarization and P-wave component, and $E^{(2)}{}_{outB}$ (z) is an OCT section image signal corresponding to the vertical polarization and S-wave component.

In this formula, A represents an OCT tomographic image signal corresponding to the horizontal polarization, where (1) and (2) are OCT tomographic image signals corresponding to the P-wave component and S-wave component, respectively. This means that $E^{(1)}{}_{outA}$ (z) represents an OCT tomographic image signal corresponding to the horizontal polarization and P-wave component, while $E^{(2)}{}_{outA}$ (z) represents an OCT tomographic image signal corresponding to the horizontal polarization and S-wave component.

On the other hand, B represents an OCT tomographic image signal corresponding to the vertical polarization, where (1) and (2) are OCT tomographic image signals corresponding to the P-wave component and S-wave component, respectively. This means that $E^{(1)}{}_{outB}$ (z) represents an OCT tomographic image signal corresponding to the vertical polarization and P-wave component, while $E^{(2)}{}_{outB}$ (z) represents an OCT tomographic image signal corresponding to the vertical polarization and S-wave component.

As explained above, OCT tomographic image signals corresponding to the horizontal polarization and P-wave component, horizontal polarization and S-wave component, vertical polarization and P-wave component, and vertical polarization and S-wave component, respectively, are shown as a matrix.

Here, $\theta_1$, $\theta_2$, and $\theta_3$ represent the phase offsets of $E^{(2)}{}_{outA}$ (z), $E^{(1)}{}_{outB}$ (z), and $E^{(2)}{}_{outB}$ (z) relative to $E^{(1)}{}_{outA}$ (z), respectively, which are not dependent on the depth direction, and this assumption that any depth-direction change in the double-refraction component of the phase can be ignored is equivalent to the approximation that the assumed double refraction property of the measuring target is sufficiently small in the normal non-polarization intensity OCT (OCT not utilizing polarization).

In this coherent coupling, $\theta_1$, $\theta_2$, and $\theta_3$ are expressed by the formula (Mathematical Formula 20) below.

$$\theta_1 \equiv \mathrm{Arg}\left[\sum_z E_{outA}^{(2)}(z)E_{outA}^{(1)}(z)^*\right]$$ [Mathematical Formula 20]

$$\theta_2 \equiv \mathrm{Arg}\left[\sum_z E_{outB}^{(1)}(z)E_{outA}^{(1)}(z)^*\right]$$

$$\theta_3 \equiv \mathrm{Arg}\left[\sum_z E_{outB}^{(2)}(z)E_{outA}^{(1)}(z)^*\right]$$

Here, Σ with the subscript z represents a sum of pixels in the depth direction. Arg is a function that gives a phase component as its argument. In other words, Arg [x] is a function that gives a phase component of complex number x (also referred to as "angle of deviation"). $E^{(1)}_{outA}$ (z)* indicates a complex conjugation of $E^{(1)}_{outA}$ (z) (the same applies to the other formulas hereinafter). It should be noted that ≡ signifies that the symbol in the left term is defined in the right term, used to mean the same thing as = (equal sign).

As for the coherent coupling mentioned above, the average ($E_{out}$ (z) with the upper line) is defined by the formula (Mathematical Formula 21) below using the coherent coupling $E_{out}$ (z) of matrix elements as well as $\theta_1$, $\theta_2$, and $\theta_3$. According to this formula, averaging the respective elements of the Jones matrix gives intensity OCT images. Here, the upper line of $E_{out}$ (z) means an average.

$$\overline{E_{out}}(z) = \frac{1}{4}[E_{outA}^{(1)}(z) + e^{-i\theta_1}E_{outA}^{(2)}(z) + e^{-i\theta_2}E_{outB}^{(1)}(z) + e^{-i\theta_3}E_{outB}^{(2)}(z)]$$ [Mathematical Formula 21]

These coupled signals represent sums of de-randomized phases of complex OCT signals, which means that stronger sensitivity can be obtained compared to the conventional method where square intensities of phase signals including random ones are summed up, and that higher resolution can be obtained when the present invention is applied to Doppler phase shift measurement as described later.

Scattered OCT images (OCT images based on scattered and reflected light from the measuring target (normal intensity OCT images)) based on the combined signals with stronger sensitivity as described above, can be obtained by the formula (Mathematical Formula 22) below using a coherent matrix element.

$$\bar{I}(z, j) = |\overline{E_{out}}(z, j)|^2$$ [Mathematical Formula 22]

Also, data from multiple B-scans may be coherently averaged to obtain scattered OCT images of even higher quality. This is expressed by the formula (Mathematical Formula 23) below.

$$\bar{I}(z, j) = \sum_{j=m_0}^{m_0+m-1} \overline{E_{out}}(z, j)\exp(-i\phi_b(j))$$ [Mathematical Formula 23]

FIG. 4 (*a*) shows an OCT image of the choroidal vessels present at a position deeper than the retina, obtained by the Jones matrix OCT system 1 pertaining to the present invention as a result of the aforementioned formula.

Apparently this image has clearer contrast than the contrast image of the same choroidal vessels obtained by angiography of the conventional indocyanine green angiography (ICGA) type as shown in FIG. 4 (*c*).

Next, a constitution where the present invention is applied to Doppler measurement (Doppler OCT) is explained.

Particularly in Doppler measurement where the Doppler signal (Doppler phase shift) is obtained from the phase difference of spectral interference signals obtained by two A-scans (first A-scan $A_1$ and second A-scan $A_2$ obtained by two B-scans), any jitter (fluctuation of signal waveforms in the time-axis direction and image disturbance resulting from such fluctuation) of the spectral interference signals obtained by the OCT directly affects data error in Doppler measurement data.

For this reason, B-scan is repeated to obtain A-line data at the same location at different points in time.

In general, raw data of the Doppler phase shift ΔØ (z) of an in-vivo measuring target is obtained by ΔØ (z)=(4πτ/$\lambda_c$) n$v_z$(z)+$Ø_b$.

Here, $\lambda_c$ represents the center wavelength of the light source, n represents the refractive index of the measuring target, $v_z$ (z) represents the component in the velocity optical axis direction (z) in which the measuring target flows, and $Ø_b$ represents a constant offset (bulk offset) due to the bulk motion (overall movement) of the measuring target. τ represents the time difference between the two A-scans, or specifically the time between the different B-scans here.

In the present invention, the raw Doppler shift ΔØ (z,j) is defined by the formula (Mathematical Formula 24) below using mutually conjugating coherent components.

$$\Delta\phi(z,j)=\mathrm{Arg}[\overline{E_{out}}(z,j+1)\overline{E_{out}}(z,j)^*]$$ [Mathematical Formula 24]

Here, ΔØ (z,j) represents the Doppler shift between the A-line in the jth B-scan and the A-line in the j+1th B-scan. * indicates complex conjugation. Also, the upper line of $E_{out}$ indicates an average.

The bulk offset Δ$Ø_b$ (j) can be written as the formula (Mathematical Formula 25) below using a depth-direction integral value.

$$\phi_b(j) = \mathrm{Arg}\left[\sum_{*} \overline{E_{out}}(z, j+1)\overline{E_{out}}(z, j)^*\right]$$ [Mathematical Formula 25]

Sensitivity can be improved by measuring the same point by a multiple (m) number of B-scans. This is shown in the formula (Mathematical Formula 26) below.

$$\overline{\Delta\phi}(z, j) = \mathrm{Arg}\left[\sum_{j=m_0}^{m_0+m-2} \overline{E_{out}}(z, j+1)\overline{E_{out}}(z, j)^*\exp(-i\phi_b(j))W(z, j)\right]$$ [Mathematical Formula 26]

Here, $m_0$ is the starting B-scan parameter, W (z,j) is the intensity mask defined by the formula (Mathematical Formula 27) below, and $\varepsilon^2$ is the noise floor (minimum noise) of the OCT image. This formula means that the window function W is set to 1 if the Doppler phase shift is greater than the specified quantity $\varepsilon^2$, but to 0 if the Doppler phase shift is smaller than the specified quantity so that it will be treated as noise and will not be added to data.

$$W(z, j) = \begin{cases} 1: & \overline{E_{out}}(z, j+1)\overline{E_{out}}(z, j)^* > \varepsilon^2 \\ 0: & \text{otherwise} \end{cases}.$$ [Mathematical Formula 27]

FIG. 4 (*b*) shows an OCT image of the choroidal vessels present at a position deeper than the retina, obtained by applying the Jones matrix OCT pertaining to the present invention to Doppler measurement to improve the sensitivity as a result, according to the formula above.

Apparently this image has improved sensitivity over the contrast image of the same choroidal vessels obtained by angiography of the conventional indocyanine green angiography (ICGA) type as shown in FIG. 4 (*c*).

When m=1, the above formula is rephrased as the formula (Mathematical Formula 28) below.

$$\overline{\Delta\phi}(z,j)=\mathrm{Arg}[\overline{E_{out}}(z,j+1)\overline{E_{out}}(z,j)^*\exp(-i\phi_b(j))W(z,j)]$$ [Mathematical Formula 28]

To display a Doppler image, the formula (Mathematical Formula 29) below is used which indicates the square intensity of the Doppler phase shift.

$$|\overline{\Delta\phi}(z,j)|^2$$ [Mathematical Formula 29]

(Calibration)

The wavelength-scanning light source is scanned by changing the wavelength along the temporal axis, so the jitter (fluctuation of signal waveforms in the time-axis direction and image disturbance resulting from such fluctuation) between (generated by the mismatch of) the scanning of the wavelength of the light source (timing of change in wavelength) and the timing at which data is gathered by the optical detector as spectral interference signals presents a problem.

This jitter introduces random shifting to spectral sampling and consequently becomes jitter of the spectral interference signals obtained by the OCT.

In the present invention, phase stabilization is made possible by using the polarization delay unit 21 to generate calibration signals, while also monitoring the spectral sampling jitter generating between the A-lines in different B-scans (fluctuation of the temporal phase position in the synchronization of scanning of the wavelength of the light source and A-line), where the computer functions as a compensation means to compensate for the jitter using the calibration signals by means of the image-processing program pertaining to the present invention.

The calibration signals are generated as described below using the swept source OCT 2 pertaining to the present invention. As mentioned earlier, ideally the polarization beam splitter 39 of the polarization delay unit 21 lets the P waves transmit through and reflects the S waves.

In reality, however, commercially available polarization beam splitters cannot completely separate the linearly polarized beams, and allow the P waves to mix in the reflected light. As a result, the polarization delay unit 21 behaves like Mach-Zehnder interferometers having a differential optical path length $z_d$ with each other, with respect to the P waves, and generates interference beams that function as calibration signals.

These calibration signals travel through the coupler 22 and are reflected by the calibration mirror 34 of the phase calibration unit 31, and again travel through the coupler 22 to be detected by the horizontal-balancing polarization detector 68 and vertical-balancing polarization detector 70 of the polarization-separation detection unit 14.

The tomographic images (line images for calibration) based on the calibration signals detected by the horizontal-balancing polarization detector 68 and vertical-balancing polarization detector 70, respectively, present themselves at the depth position corresponding to the aforementioned differential optical path length $z_d$, and this position is always exactly the middle point of two multiplexed signals of input polarization as shown in FIG. 2 (*a*) and FIG. 2 (*b*). This is used to compensate for the jitter (fluctuation of temporal phase position) in the synchronization of scanning of the wavelength of the light source and A-line.

Jitter compensation is explained below. When the first A-line of B-scan is used as the reference and its spectral intensity is given by $I_r$ (j) and other A-line data to be calibrated is given by $I_c$ (j), for example, then their relationship is expressed by the formula (Mathematical Formula 30) below.

$$I_r(j)=|E_r(j)+E_t(j)|^2$$

$$I_c(j)=|E_r(j-\beta_j)+E_t(j-\beta_j)|^2=I_r(j)*\delta(j-\beta_j)$$ [Mathematical Formula 30]

Here, $E_r$ (j) and $E_c$ (j) are spectral interference components based on the beams reflected by and transmitting through the polarization delay unit, where j is a B-line parameter.

* represents convolution, while $\beta_j$ indicates a relative spectral shift.

In estimating the spectral shift, first the complex conjugates of the Fourier-transformed reference A-line signal and Fourier-transformed A-line signal to be calibrated, are integrated according to the formula (Mathematical Formula 31) below.

$$\mathcal{F}[I_r(j)]\mathcal{F}[I_c(j)]^*=\mathcal{F}[I_r(j)]\mathcal{F}[I_r^*(-j)]\mathcal{F}[\delta(-j-\beta_j)]$$ [Mathematical Formula 31]

Here, F [ ] represents Fourier transformation, while the superscript * indicates complex conjugation. When the above formula is Fourier-reverse-transformed, the formula (Mathematical Formula 32) below is obtained.

[Mathematical Formula 32]

$$\begin{aligned}\mathcal{F}^{-1}[\mathcal{F}[I_r(j)]\mathcal{F}[I_c(j)]^*] &= I_r(j) * I_r^*(-j) * \delta(-j-\beta_j) \\ &= \{I_r(j) \otimes I_r(j)\} * \delta(-j-\beta_j)\end{aligned}$$

Here, the symbol consisting of a circle with an X inside represents correlation. And, in the formula (Mathematical Formula 33) below, $I_r$ (j) is an auto-correlating function and takes the maximum value at j=0, meaning that the overall maximum value is obtained when $j=-\beta_j$.

$$I_r(j)\otimes I_r(j)$$ [Mathematical Formula 33]

Accordingly, the spectral shift $\beta_j$ can be determined from the location where the signal from the above formula becomes the maximum. To raise the detection accuracy, zero-filling may be used to expand the exterior of valid data with value 0 data during Fourier transformation, as this improves the resolution in the frequency space. For example, expanding the range 16 folds allows for detection of shift in the frequency space at an accuracy of 1/16 pixel.

In the SS-OCT, the light source is linearly scanned with respect to the frequency of light. When processing the data, wave numbers must be converted to linear data, which is done through a procedure called re-scaling that involves table conversion. By preparing beforehand a frequency vs. wave number re-scaling table incorporating the aforementioned shift, jitter compensation and re-scaling can be performed in a single transformation.

The foregoing explained, based on the example, a mode for implementing the Jones matrix OCT system pertaining to the present invention as well as the program for image-processing the measured data obtained by such OCT; however, it goes without saying that the present invention is not limited to this example in any way and that various examples may be given within the scope of the technical items described in "What Is Claimed Is."

INDUSTRIAL FIELD OF APPLICATION

The Jones matrix OCT system pertaining to the present invention as well as the program for image-processing the measured data obtained by such OCT are best suited for use in non-invasive ophthalmological diagnostic systems and are especially useful in very early diagnosis of glaucoma and diabetic retinopathy based on simulated angiography and quantitative evaluation of the choroidal vessels.

DESCRIPTION OF THE SYMBOLS

1 Jones matrix OCT system
2 Swept source OCT
3 Computer
6 Light source
7 Measuring target
8 Optical isolator
11 Fiber coupler
12 Reference arm
13 Probe arm
14 Polarization-separation detection unit
17 Fiber
20 Polarization controller
21 Polarization delay unit
22 Coupler
23 Fiber collimator
24 Two-axis galvano-scanner
25 Objective lens
26 Non-spherical ophthalmological lens
31 Phase calibration unit
32 Fiber collimator
33 Lens
34 Mirror (calibration mirror)
37 Fiber collimator
38 45° linear polarizer
39 Polarization beam splitter
40 First Dove prism
41 Second Dove prism
42 Multiplexing polarization beam splitter
43 Fiber collimator
46 Fiber collimator
47 Mirror
48 Mirror
49 Fiber collimator
50 Polarization controller
54 Multiplexing beam splitter
55 Polarization controller
56 Fiber collimator
57 Fiber collimator
58 45° linear polarizer
61 First optical path
62 Second optical path
63 First polarization beam splitter
64 Second polarization beam splitter
67 Fiber collimator
68 Horizontal-balancing polarization detector
69 Fiber collimator
70 Vertical-balancing polarization detector
74 Fiber collimator
75 Fiber collimator
81 Input part
82 Output part
83 CPU
84 Memory
85 Data bus
93 OCT
94 Light source
95 Collimator lens
96 Beam splitter
97 Objective lens
98 Measuring target
99 Objective lens
100 Reference mirror
101 Condensing lens
102 Optical detector

What is claimed is:

1. A Jones matrix OCT system having:

a wavelength-scanning light source;

a coupler that splits a light from the wavelength-scanning light source into two optical paths;

a reference arm provided along one of the two optical paths, to reflect one split light using a reference mirror and thus generate reference light;

a probe arm provided along the other of the two optical paths, to irradiate the other split light onto a measuring target which then reflects the other split light and thus generates object light;

a polarization-separation detection unit comprising a multiplexing beam splitter that superimposes the reference light and the object light to generate spectral interference beams and then detect the spectral interference beams using optical detectors; and a computer that generates tomographic images of the measuring target based on the spectral interference beams detected by the polarization-separation detection unit;

the Jones matrix OCT system characterized in that:

the probe arm has a polarization delay unit that linearly polarizes the other split light and then splits it into S-wave component and P-wave component, where the S-wave component and P-wave component are superimposed with each other through optical paths of different optical path lengths, respectively;

wherein the polarization-separation detection unit obtains four spectral interference signals by using the optical detectors by detecting two different spectral interference beams in a depth direction of the measuring target wherein the two different spectral interference beams correspond to S-wave component and P-wave component, respectively, among vertically polarized components of the spectral interference beams generated by the multiplexing beam splitter, as well as two different spectral interference beams in the depth direction of the measuring target wherein the two different spectral interference beams correspond to the S-wave component and P-wave component, respectively, among horizontally polarized components of the spectral interference beams generated by the multiplexing beam splitter; and the computer generates tomographic images in the depth direction of the measuring target from the four spectral interference signals transferred to the computer, and generates tomographic images of higher resolution by obtaining coherent coupling as a matrix of the four spectral interference signals and by further combining the four spectral interference signals after de-randomizing their phases to obtain matrix coherent elements, wherein:

the coherent coupling, $E_{out}$ (z), of matrix elements is expressed by the formula below as the matrix of the four spectral interference signals expressed by depth (z):

$$E_{out}(z) = \begin{bmatrix} E^{(1)}_{outA}(z) & E^{(2)}_{outA}(z) \\ E^{(1)}_{outB}(z) & E^{(2)}_{outB}(z) \end{bmatrix} \simeq \begin{bmatrix} E^{(1)}_{outA}(z) & e^{j\theta_1} E^{(1)}_{outA}(z) \\ e^{j\theta_2} E^{(1)}_{outA}(z) & e^{j\theta_3} E^{(1)}_{outA}(z) \end{bmatrix}$$

wherein $E^{(1)}_{outA}$ (z) is an OCT section image signal corresponding to the horizontal polarization P-wave component, $E^{(2)}_{outA}$ (z) is an OCT section image signal corresponding to the horizontal polarization S-wave component, $E^{(1)}_{outB}$ (z) is an OCT section image signal corresponding to the vertical polarization P-wave component, and $E^{(2)}_{outB}$ (z) is an OCT section image signal corresponding to the vertical polarization S-wave component, $\theta_1$, $\theta_2$, and $\theta_3$ represent phase offsets of $E^{(2)}_{outA}$ (z), $E^{(1)}_{outB}$ (z), and $E^{(2)}_{outB}$ (z) relative to $E^{(1)}_{outA}$ (z), respectively, which are not dependent on the depth direction and are expressed by the formula below:

$$\theta_1 \equiv \mathrm{Arg}\left[\sum_z E^{(2)}_{outA}(z)E^{(1)}_{outA}(z)^*\right]$$

$$\theta_2 \equiv \mathrm{Arg}\left[\sum_z E^{(1)}_{outB}(z)E^{(1)}_{outA}(z)^*\right]$$

$$\theta_3 \equiv \mathrm{Arg}\left[\sum_z E^{(2)}_{outB}(z)E^{(1)}_{outA}(z)^*\right]$$

wherein Σ with the subscript z represents a sum of pixels in the depth direction, Arg [x] is a function that gives a phase component of complex number x, * indicates a complex conjugation wherein $E^{(1)}_{outA}$ (z)* indicates a complex conjugation of $E^{(1)}_{outA}$ (z), and ≡ indicates that the symbol in the left term is defined in the right term and is used to mean the same as = (equal sign), the de-randomizing of phases is averaging the respective elements of the matrix as defined in the formula below:

$$\overline{E_{out}}(z)=\tfrac{1}{4}[E_{outA}^{(1)}(z)+e^{-i\theta_1}E_{outA}^{(2)}(z)+e^{-i\theta_2}E_{outB}^{(1)}(z)+e^{-i\theta_3}E_{outB}^{(2)}(z)]$$

wherein the upper line of $E_{out}$ (z) means an average, and the tomographic images of higher resolution expressed by $\bar{I}$(z,j) is obtained by the formula below:

$$\bar{I}(z,j)=|\overline{E_{out}}(z,j)|^2$$

2. A Jones matrix OCT system according to claim 1, characterized in that the computer is constituted in a manner displaying a Doppler image as the tomographic images of higher resolution by calculating a formula $$|\overline{\Delta\phi}(z,j)|^2$$

indicating a square intensity of a Doppler shift, based on a definition that a Doppler shift Δφ (z,j) between an A-line in a jth B-scan and an A-line in a j+1th B-scan is represented by mutually conjugating coherent components as show in the formula below:

$$\Delta\phi(z,j)=\mathrm{Arg}[\overline{E_{out}}(z,j+1)\overline{E_{out}}(z,j)^*]$$

where a same point is measured by repeating a B-scan m times to obtain an averaged Doppler shift expressed in the formula below, which is then applied to Doppler measurement to improve a sensitivity of Doppler measurement;

$$\overline{\Delta\phi}(z,j) = \mathrm{Arg}\left[\sum_{j=m_0}^{m_0+m-2} \overline{E_{out}}(z,j+1)\overline{E_{out}}(z,j)^*\exp(-i\phi_b(j))W(z,j)\right]$$

wherein $m_0$ is a starting B-scan parameter, W (z,j) is an intensity mask defined by the formula below, and $\varepsilon^2$ is a noise floor or minimum noise of OCT images, wherein window function W is set to 1 if the Doppler shift is greater than the specified quantity $\varepsilon^2$, but to 0 if the Doppler shift is smaller than the specified quantity, treating the Doppler shift as noise which is not be added to data:

$$W(z,j) = \begin{cases} 1: & \overline{E_{out}}(z,j+1)\overline{E_{out}}(z,j)^* > \varepsilon^2 \\ 0: & \text{otherwise} \end{cases}.$$

3. A Jones matrix OCT system according to claim 2, characterized in that: a phase calibration unit having a calibration mirror is provided in an optical path branching from the other of the two optical paths leading to the measuring target via a second coupler;

the calibration mirror reflects interference beams entering the calibration unit, which have been generated at the polarization delay unit due to interference caused by differential optical path lengths of the P waves and S waves, and sends the interference beams to the polarization-separation detection unit via the second coupler to be superimposed with the reference light into interference beams that function as calibration signals;

a horizontal-balancing polarization detector and a vertical-balancing polarization detector provided in the polarization-separation detection unit, respectively, detect the interference beams that function as calibration signals; and the computer uses these calibration signals to compensate a jitter generated in synchronization between a wavelength scan of the wavelength-scanning light source and an A-scan which is a scan of the measuring target in the depth direction.

4. A Jones matrix OCT system according to claim 1, characterized in that the computer is constituted in a manner obtaining OCT images based on a scattered and reflected light from the measuring target, wherein the OCT images are high-quality scattered OCT images which are obtained by calculating a coherent average of data from multiple B-scans and expressed by $\bar{I}$(z,j) in the formula below:

$$\bar{I}(z,j) = \sum_{j=m_0}^{m_0+m-1} \overline{E_{out}}(z,j)\exp(-i\phi_b(j))$$

wherein m is the number of repetitions of B-scan.

5. A Jones matrix OCT system according to claim 4, characterized in that: a phase calibration unit having a calibration mirror is provided in an optical path branching from the other of the two optical paths leading to the measuring target via a second coupler;

the calibration mirror reflects interference beams entering the calibration unit, which have been generated at the polarization delay unit due to interference caused by differential optical path lengths of the P waves and S waves, and sends the interference beams to the polarization-separation detection unit via the second coupler to be superimposed with the reference light into interference beams that function as calibration signals;

a horizontal-balancing polarization detector and a vertical-balancing polarization detector provided in the polarization-separation detection unit, respectively, detect the interference beams that function as calibration signals; and the computer uses these calibration signals to compensate a jitter generated in synchronization between a wavelength scan of the wavelength-scanning light source and an A-scan which is a scan of the measuring target in the depth direction.

6. A Jones matrix OCT system according to claim 1, characterized in that: a phase calibration unit having a calibration mirror is provided in an optical path branching from the other of the two optical paths leading to the measuring target via a second coupler;

the calibration mirror reflects interference beams entering the calibration unit, which have been generated at the polarization delay unit due to interference caused by differential optical path lengths of the P waves and S waves, and sends the interference beams to the polarization-separation detection unit via the second coupler to be superimposed with the reference light into interference beams that function as calibration signals;

a horizontal-balancing polarization detector and a vertical-balancing polarization detector provided in the polarization-separation detection unit, respectively, detect the interference beams that function as calibration signals; and the computer uses these calibration signals to compensate a jitter generated in synchronization between a wavelength scan of the wavelength-scanning light source and an A-scan which is a scan of the measuring target in the depth direction.

7. A non-transitory computer readable storage medium storing a program installed in a computer of a Jones matrix OCT system to generate tomographic images of a measuring target based on spectral interference beams detected by an optical detector, where the Jones matrix OCT system has:

a wavelength-scanning light source;

a coupler that splits a light from the wavelength-scanning light source into two optical paths; a reference arm provided along one of the two optical paths, to reflect one split light using a reference mirror and thus generate reference light;

a probe arm provided along the other of the two optical paths, to irradiate the other split light onto a measuring target which then reflects the other split light and thus generates object light;

a polarization-separation detection unit comprising a multiplexing beam splitter that superimposes the reference light and the object light to generate spectral interference beams and then detect the spectral interference beams using optical detectors; and the computer;

wherein the probe arm has a polarization delay unit that linearly polarizes the other split light and then splits it into S-wave component and P-wave component, where the S-wave component and P-wave component are superimposed with each other through optical paths of different optical path lengths, respectively;

the polarization-separation detection unit obtains four spectral interference signals by using the optical detectors by detecting two different spectral interference beams in a depth direction of the measuring target wherein the two different spectral interference beams correspond to S-wave component and P-wave component, respectively, among vertically polarized components of the spectral interference beams generated by the multiplexing beam splitter, as well as two different spectral interference beams in the depth direction of the measuring target wherein the two different spectral interference beams correspond to the S-wave component and P-wave component, respectively, among horizontally polarized components of the spectral interference beams generated by the multiplexing beam splitter; and the program is characterized in that it allows the computer to function as an image-processing means that generates tomographic images in the depth direction of the measuring target from the four spectral interference signals transferred to the computer, and also generates tomographic images of higher resolution by obtaining coherent coupling from a matrix of the four spectral interference signals and by also obtaining coherent elements that have been combined after de-randomizing phases of the four spectral interference signals, wherein:

the coherent coupling, $E_{out}$ (z), of matrix elements is expressed by the formula below as the matrix of the four spectral interference signals expressed by depth (z):

$$E_{out}(z) = \begin{bmatrix} E^{(1)}_{outA}(z) & E^{(2)}_{outA}(z) \\ E^{(1)}_{outB}(z) & E^{(2)}_{outB}(z) \end{bmatrix} \simeq \begin{bmatrix} E^{(1)}_{outA}(z) & e^{j\theta_1} E^{(1)}_{outA}(z) \\ e^{j\theta_2} E^{(1)}_{outA}(z) & e^{j\theta_3} E^{(1)}_{outA}(z) \end{bmatrix}$$

wherein $E^{(1)}_{outA}$ (z) is an OCT section image signal corresponding to the horizontal polarization P-wave component, $E^{(2)}_{outA}$ (z) is an OCT section image signal corresponding to the horizontal polarization S-wave component, $E^{(1)}_{outB}$ (z) is an OCT section image signal corresponding to the vertical polarization P-wave component, and $E^{(2)}_{outB}$ (z) is an OCT section image signal corresponding to the vertical polarization S-wave component, $\theta_1$, $\theta_2$, and $\theta_3$ represent phase offsets of $E^{(2)}_{outA}$ (z), $E^{(1)}_{outB}$ (z), and $E^{(2)}_{outB}$ (z) relative to $E^{(1)}_{outA}$ (z), respectively, which are not dependent on the depth direction and are expressed by the formula below:

$$\theta_1 \equiv \mathrm{Arg}\left[\sum_z E^{(2)}_{outA}(z) E^{(1)}_{outA}(z)^*\right]$$

$$\theta_2 \equiv \mathrm{Arg}\left[\sum_z E^{(1)}_{outB}(z) E^{(1)}_{outA}(z)^*\right]$$

$$\theta_3 \equiv \mathrm{Arg}\left[\sum_z E^{(2)}_{outB}(z) E^{(1)}_{outA}(z)^*\right]$$

wherein Σ with the subscript z represents a sum of pixels in the depth direction, Arg [x] is a function that gives a phase component of complex number x, * indicates a complex conjugation wherein $E^{(1)}_{outA}$ (z)* indicates a complex conjugation of $E^{(1)}_{outA}$ (z), and ≡ indicates that the symbol in the left term is defined in the right term and is used to mean the same as = (equal sign), the de-randomizing of phases is averaging the respective elements of the matrix as defined in the formula below:

$$\overline{E_{out}}(z) = \frac{1}{4}[E^{(1)}_{outA}(z) + e^{-i\theta_1}E^{(2)}_{outA}(z) + e^{-i\theta_2}E^{(1)}_{outB}(z) + e^{-i\theta_3}E^{(2)}_{outB}(z)]$$

wherein the upper line of $E_{out}$ (z) means an average, and the tomographic images of higher resolution expressed by $\overline{I}$(z,j) is obtained by the formula below:

$$\overline{I}(z, j) = |\overline{E_{out}}(z, j)|^2.$$

8. A computer readable non-transitory medium storing a program according to claim 7, characterized in that the program allows the computer to function as the image-processing means that displays a Doppler image as the tomographic images of higher resolution by calculating a formula $$|\overline{\Delta\phi}(z,j)|^2$$

indicating a square intensity of a Doppler shift, based on a definition that a Doppler shift Δϕ (z,j) between an A-line in a jth B-scan and an A-line in a j+1th B-scan is represented by mutually conjugating coherent components as show in the formula below:

$$\Delta\phi(z,j)=\text{Arg}[\overline{E_{out}}(z,j+1)\overline{E_{out}}(z,j)^*]$$

and also improves a sensitivity of Doppler measurement by measuring a same point by repeating a B-scan m times to obtain an averaged Doppler shift expressed in the formula below, which is then applied to Doppler measurement to improve a sensitivity of Doppler measurement:

$$\overline{\Delta\phi}(z, f) = \text{Arg}\left[\sum_{j=m_0}^{m_0+m-2} \overline{E_{out}}(z, j+1)\overline{E_{out}}(z, j)^* \exp(-i\phi_b(j))W(z, j)\right]$$

wherein $m_0$ is a starting B-scan parameter, W (z,j) is an intensity mask defined by the formula below, and $\varepsilon^2$ is a noise floor or minimum noise of OCT images, wherein window function W is set to 1 if the Doppler shift is greater than the specified quantity $\varepsilon^2$, but to 0 if the Doppler shift is smaller than the specified quantity, treating the Doppler shift as noise which is not be added to data:

$$W(z, j) = \begin{cases} 1: & \overline{E_{out}}(z, j+1)\overline{E_{out}}(z, j)^* > \varepsilon^2 \\ 0: & \text{otherwise} \end{cases}.$$

9. A non-transitory computer readable storage medium storing a program according to claim 7, characterized in that the program allows the computer to function as the image-processing means that obtains OCT images based on a scattered and reflected light from the measuring target using coherent matrix components, and can also obtain wherein the OCT images are high-quality scattered OCT images which are obtained by calculating a coherent average of data from multiple B-scans and expressed by $\overline{I}$(z,j) in the formula below:

$$\overline{I}(z, j) = \sum_{j=m_0}^{m_0+m-1} \overline{E_{out}}(z, j)\exp(-i\phi_b(j))$$

wherein m is the number of repetitions of B-scan.

* * * * *

UNITED STATES PATENT AND TRADEMARK OFFICE

CERTIFICATE OF CORRECTION

PATENT NO. : 10,470,663 B2
APPLICATION NO. : 14/892192
DATED : November 12, 2019
INVENTOR(S) : Yoshiaki Yasuno, Myeong Jin Ju and Masahide Itoh It is certified that error appears in the above-identified patent and that said Letters Patent is hereby corrected as shown below:

In the Claims

At Column 26, Line 26, in Claim 9, please delete the phrase "and can also obtain"

Signed and Sealed this
Twenty-third Day of June, 2020

Andrei Iancu
*Director of the United States Patent and Trademark Office*